United States Patent [19]

Garcia

[11] 4,351,185

[45] Sep. 28, 1982

[54] HIGH TEMPERATURE PENETRANT SYSTEM

[75] Inventor: Vilma A. Garcia, Westchester, Ill.

[73] Assignee: Magnaflux Corporation, Chicago, Ill.

[21] Appl. No.: 228,604

[22] Filed: Jan. 26, 1981

[51] Int. Cl.³ .................. G01B 5/28; G01N 19/08
[52] U.S. Cl. ...................................... 73/104; 106/19
[58] Field of Search ............... 73/105, 104; 106/19; 73/358

[56] References Cited

U.S. PATENT DOCUMENTS

| | | | |
|---|---|---|---|
| 2,020,676 | 11/1935 | Ellis | 73/358 |
| 2,396,219 | 3/1946 | Weagle | 106/19 |
| 3,491,043 | 1/1970 | Zmitrovis | 106/19 |
| 3,607,333 | 9/1971 | Alburger | 106/19 |
| 3,904,545 | 9/1975 | Molina | 73/104 |

Primary Examiner—S. Clement Swisher
Attorney, Agent, or Firm—Hill, Van Santen, Steadman, Chiara & Simpson

[57] ABSTRACT

A method and composition for non-destructive testing using the dye penetrant technique, and adapting the use of this technique at high temperatures. The invention is involved with using a marking crayon which includes a carrier composed of a solid which melts at a temperature below the temperature at which the workpiece is to be inspected and a visible or fluorescent dye. Upon application of the crayon to a hot workpiece, the solid penetrant composition becomes molten and the visible or fluorescent dye penetrates into any flaws in the surface in the usual manner. A remover, also consisting of a crayon composition, is used to remove excess penetrant, leaving only penetrant entrapped in the flaws. Upon removal of the excess penetrant and remover, the entrapped penetrant deposits are drawn to surface by the application of a finely divided developer either in dry form or as an aerosol. Inspection of the piece is then carried out under visible or ultraviolet light, depending upon the nature of the penetrant.

7 Claims, 6 Drawing Figures

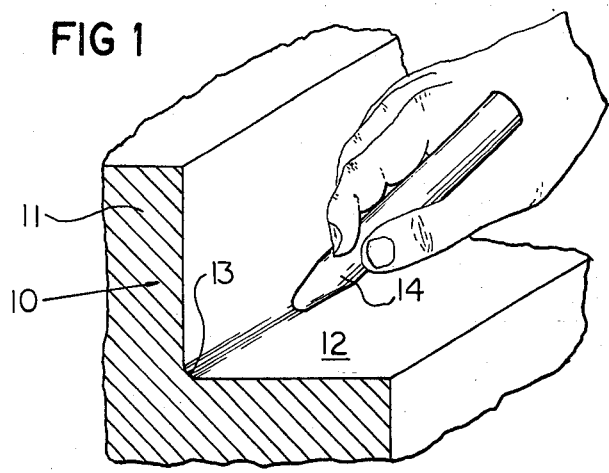
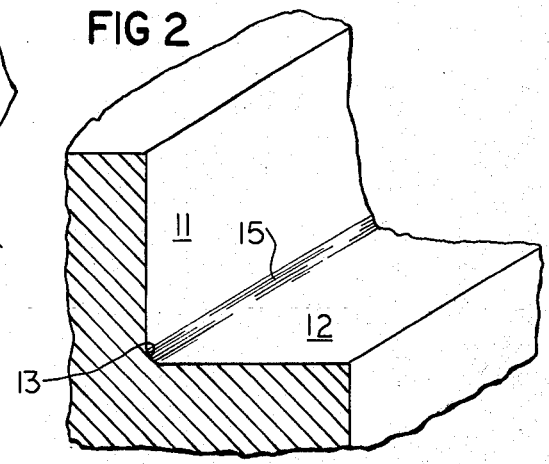
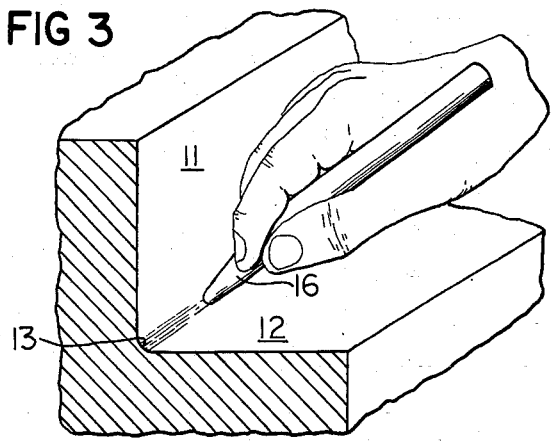
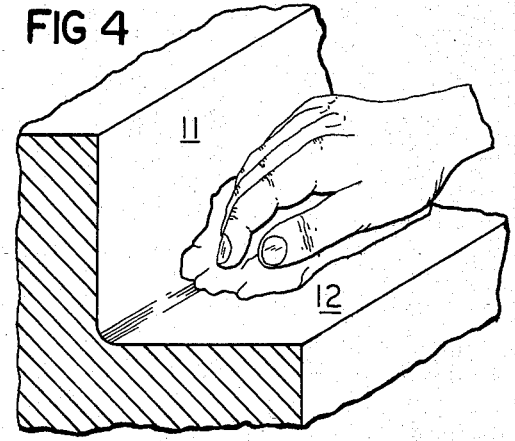
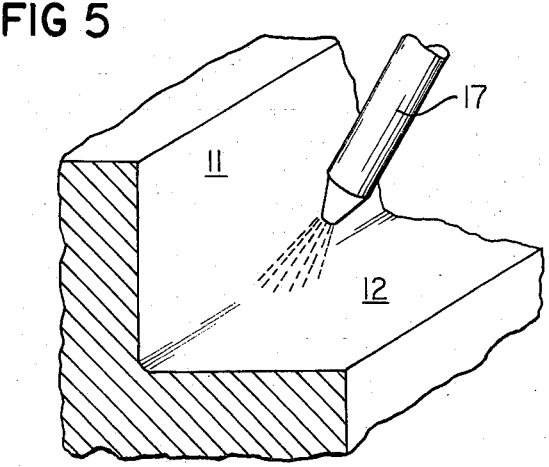
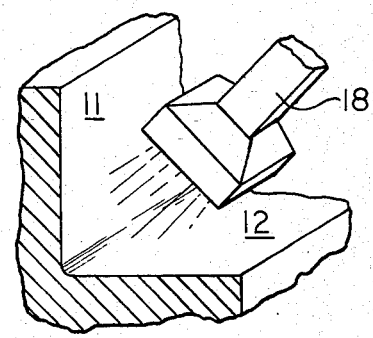

HIGH TEMPERATURE PENETRANT SYSTEM

BACKGROUND OF THE INVENTION

1. Field of the Invention

The present invention is in the field of nondestructive testing utilizing the penetrant inspection technique, and provides an improved penetrant composition in the form of a crayon and a remover in the form of a crayon, both being adapted for use of the penetrant inspection technique at elevated temperatures.

2. Description of the Prior Art

The standard penetrant inspection technique has been highly developed for many decades. Basically, the technique consists in first cleaning the workpiece to be inspected to remove surface films and oxides and then flooding the area to be inspected with a penetrant composition. Such composition for normal use consists of a light hydrocarbon oil or an emulsifiable oil containing either a visible penetrant, usually a red dye, or a fluorescent dye. The penetrant is allowed to dwell on the surface of the workpiece for a sufficient time to enable it to seep into surface discontinuities or flaws which extend to the surface. The excess penetrant is then removed by wiping, or emulsification in the case of a hydrocarbon oil, or by washing with water in the case of an emulsifiable penetrant composition. After drying, a developer is applied to the surface which may take the form of finely divided solid particles or a dispersion of solid particles in a liquid or an aerosol. The deposit of finely divided particles serves to immobilize the penetrant being exuded from the flaw and to render the penetrant contrastingly visible to the power deposit. Inspection of the piece is then done under ordinary white light in the case of a visible penetrant or under ultraviolet irradiation when using the more sensitive fluorescent dyes.

The penetrant inspection technique has become a mainstay of American industry. It does have some limitations, however, particularly with respect to temperature limitations. Both visible and fluorescent dye materials lose their brilliance and in some cases their characteristic color completely when operating at temperatures in excess of about 200° F. (93° C.). Yet, it would be highly desirable to use this type of inspection on metal shapes in the rolling mill, or newly welded workpieces which are at a temperature substantially in excess of the prior limiting temperature.

SUMMARY OF THE INVENTION

The present invention provides an improved marking crayon which is suitable for use in the non-destructive testing of a workpiece at an elevated temperature, and the process for non-destructive testing involving the use of such a crayon. Specifically, the crayon may consist of a carrier composed of a solid which melts at a temperature below the temperature at which the workpiece is to be inspected and contains a visible or fluorescent dye dissolved therein. The carrier may include a waxy solid and a resin. Particularly good results are obtained through the use of a heat stable fluorescent dye known under the Colour Index generic name of Solvent Green 5 (C.I. 59075). This material has been found to retain its fluorescent properties at temperatures up to 500° F. (260° C.) making it ideally suited for the method of the present invention.

In performing the method of the present invention, the improved crayon of the present invention is applied to a clean workpiece so that it becomes molten upon contact, causing the penetrant to begin moving into surface flaws. After a short dwell time, excess penetrant is removed by means of a remover crayon usually consisting of the same waxy type solid which is contained in the penetrant crayon. The remover, in turn, is removed mechanically. Then a developing composition is promptly applied to the site, the developer consisting of dry particles such as silica aerogel particles or talc, preferably by electrostatic deposition or the particles may be applied in an aerosol. The inspection of the piece is then carried out in the usual way under white light in the case of a visible penetrant, and under ultraviolet or "black" light in the case of a fluorescent type penetrant.

BRIEF DESCRIPTION OF THE DRAWINGS

A further description of the present invention will be made in conjunction with the attached sheet of drawings which illustrate a typical sequence in using the method of the present invention.

FIG. 1 is a view in perspective illustrating the manner in which the penetrant is originally applied from the crayon;

FIG. 2 is a view similar to FIG. 1 but showing the penetrant in its molten condition on the workpiece;

FIG. 3 is a view in perspective showing the manner in which excess penetrant can be removed by the use of a remover crayon;

FIG. 4 illustrates the step of removing excess cleaner;

FIG. 5 illustrates the step of spraying on a uniform film of developer onto the cleaned surface; and FIG. 6 is a view of the inspection process in which flaws are detected by inspection under ultraviolet irradiation.

DESCRIPTION OF THE PREFERRED EMBODIMENTS

In the drawings, there is illustrated a procedure for detecting flaws in a workpiece 10 having a vertical wall 11 and a horizontal wall 12 joined by a radius 13. The first step consists in estimating the temperature of the part using a surface thermometer, a decal, and/or a temperature stick. When the approximate temperature is determined, a penetrant crayon having a melting range below the temperature of the workpiece is applied to the area to be inspected, as illustrated by the crayon 14 in FIG. 1. The penetrant composition becomes molten quite rapidly, leaving a molten deposit illustrated at reference numeral 15 in FIG. 2. The penetrant is sufficiently fluid to find its way into surface cracks and into defects which have an opening to the surface. Excess penetrant can then be removed using a paper towel, an asbestos or cotton cloth, or the like.

FIG. 3 illustrates the succeeding step of applying a remover crayon 16 to the penetrant treated radius to eliminate further any surface penetrant which could obscure the red or fluorescent background that could be left on the surface. The excess cleaner is wiped off immediately as illustrated in FIG. 4 of the drawings with a clean paper towel or the like.

The succeeding step is that of applying a developer to the area in which the penetrant has become lodged so as to draw the liquid penetrant up to the surface by capillary action. This step is illustrated by means of an aerosol spray device 17 applying a suspension of finely divided developer particles such as talc, or the like, to the area to be inspected. The final step consists in observing the indications by means of a suitable light source which may be white light in the case of a visible penetrant, or an ultraviolet lamp 18 in the case of a fluorescent penetrant.

SPECIFIC EXAMPLES

A crayon was made up to operate with a temperature range of 370° to 500° F. (188° to 260° C.) and having the following composition:

"Pentalyn K" synthetic resin, m.p. 370° F. (188° C.), (a pentaerythritol ester of dimeric acids): 50 parts by weight "Versar" synthetic wax, m.p. 170° F. (77° C.): 50 parts by weight Calco Rhodamine Base DY (visible dye): 8 parts by weight.

A fluorescent type penetrant for the same temperature operating range was produced with the following composition:

"Multiwax X-145 A", m.p. 150° F. (66° C.), (a paraffin microcrystalline wax derived from petroleum: 100 parts by weight "Pentalyn K" synthetic resin: 40 parts by weight Solvent Green 5: 6 parts by weight.

For both of the above-identified penetrant crayons, the remover can conveniently consist of solid "Biwax E-715" which is a mixture of synthetic polyolefin and microcrystalline waxes derived from petroleum, having a melting point of 290° F. (143° C.).

A crayon suitable for use at temperatures in the range of about 180° to 370° F. (82° to 188° C.) was made up as follows:

"Versar" synthetic wax: 100 parts by weight

Calco Rhodamine Base DY: 8 parts by weight.

A fluorescent counterpart for operating in the last-named range was made up as follows:

"Multiwax X-145A": 140 parts by weight

Solvent Green 5: 6 parts by weight.

For the lower temperature penetrant crayons, a suitable remover is "Multiwax X-145 A".

The crayons can be easily manufactured by heating the wax to its melting temperature, adding the resin, if any, to the molten wax and raising the temperature to the melting point of the resin. The mixture is mixed to form a homogeneous solution without overheating. The dye is then dissolved by mixing into the molten mixture. After dissolution, the completed mixture is poured into tubes and let stand to set.

About 1 to 3 minutes penetration time is usually adequate, depending on the crack size and contamination. In addition to using an aerosol type developer it is also possible to apply the dry developer electrostatically as by means of a "Statiflux" gun. Aerosols containing sulfur or chlorine should generally be avoided to minimize the danger of contaminating the hot surface.

A high temperature developer can be made up as follows:

Calcium carbonate—45.5 grams

Titanium dioxide—13.2 grams

Silica powder—5.0 grams

Zinc stearate—5.0 grams

"Pentalyn K" resin—5.0 grams

"Surfonic N95"—15.0 grams (non-ionic surfactant)

1, 1, 1 trichloroethane—598.0 ml.

It should be evident that various modifications can be made to the described embodiments without departing from the scope of the present invention.

I claim as my invention:

1. A method for the non-destructive testing of a workpiece for surface flaws at an elevated temperature which comprises marking areas of said workpiece with a crayon comprising a carrier which melts at a temperature below said elevated temperature having dissolved therein a dye which is liquid at said temperature and is contrastingly visible to said workpiece at said elevated temperature, and applying a developer at said elevated temperature to the marked areas to thereby draw up dye which has been lodged in surface flaws, and inspecting the workpiece.

2. A method according to claim 1 which includes the step of:
applying a solid remover crayon to the molten penetrant composition to remove excess penetrant before application of said developer, said remover crayon including a solvent for the dye of said penetrant.

3. A method according to claim 1 in which:
said fluorescent dye is Solvent Green 5.

4. A method according to claim 1 in which said carrier includes a waxy solid having a melting point not in excess of 400° F. (204° C.).

5. A method according to claim 1 in which said carrier includes a synthetic wax.

6. A marking crayon suitable for use in the non-destructive testing of a workpiece at an elevated temperature which comprises:
a carrier composed of a solid waxy material having a melting point below said elevated temperature, and a dye dissolved therein which retains its dye properties at least to about 500° F. (260° C.),
said crayon being rendered completely molten at said elevated temperature, permitting the dissolved dye to penetrate into flaws with which it comes into contact.

7. A crayon according to claim 6 in which:
said dye is Solvent Green 5.

* * * * *